US006689057B1

(12) United States Patent
Shinsel et al.

(10) Patent No.: US 6,689,057 B1
(45) Date of Patent: Feb. 10, 2004

(54) METHOD AND APPARATUS FOR COMPRESSING CALORIE BURN CALCULATION DATA USING POLYNOMIAL COEFFICIENTS

(75) Inventors: David W. Shinsel, Portland, OR (US); Matthew C. Curfman, Hillsboro, OR (US)

(73) Assignee: Intel Corporation, Santa Clara, CA (US)

(*) Notice: Subject to any disclaimer, the term of this patent is extended or adjusted under 35 U.S.C. 154(b) by 548 days.

(21) Appl. No.: 09/773,174

(22) Filed: Jan. 30, 2001

(51) Int. Cl.[7] .................................................. A61B 5/00
(52) U.S. Cl. .............................................. 600/300; 482/8
(58) Field of Search ........................... 482/4, 8–9, 900, 482/901; 600/300–301, 481, 587, 500, 502, 595; 128/897, 898, 900, 903–905, 920–921; 709/200, 203, 217; 702/19; 705/2–4

(56) References Cited

U.S. PATENT DOCUMENTS 3,984,666 A  * 10/1976  Barron ........................... 482/8
5,976,083 A  * 11/1999  Richardson et al. ......... 600/300
6,013,009 A  *  1/2000  Karkanen ....................... 482/9
6,135,951 A  * 10/2000  Richardson et al. ......... 600/300
6,478,736 B1 * 11/2002  Mault .......................... 600/300

* cited by examiner

*Primary Examiner*—Max F. Hindenburg
*Assistant Examiner*—Michael Astorino
(74) *Attorney, Agent, or Firm*—Blakely, Sokoloff, Taylor & Zafman LLP

(57) ABSTRACT

A device is presented including a processor. A memory is connected to the processor. The processor calculates calorie burn. The memory has a many data objects for storing data accessed by an application program that is executed on the processor. The data objects include a first data structure that is stored in one of the many data objects. The data structure includes a formatted exercise data block used by the application program. The formatted exercise data block includes many formatted exercise intensity data blocks that have polynomial parameters. Also, a second data structure is stored in another one of the many data objects. This data structure includes a formatted calorie calculation block used by the application program.

27 Claims, 6 Drawing Sheets

| Exercise Type ID | Exercise Class | CaloriesPerMinutePerKg= | Value 1 | Value 2 |
|---|---|---|---|---|
| 1 | Cardio (Time only) | A | TimeInMinutes | |
| 2 | Cardio (Time&Intensity) | A + (B*Val2) + (C*Val2^2) | TimeInMinutes | Intensity |
| 3 | Cardio (Time&Distance1) | A + (B*(Val1 / Val2)) + (C*(Val1 / Val2) ^2) | TimeInMinutes | Distance |
| 4 | Cardio (Pedometer) | A + (B*(Val1 / Val2)) + (C*(Val1 / Val2) ^2) | TimeInMinutes | Distance |
| 5 | Strength (Bodyweight) | N/A | Reps | |
| 6 | Strength (with weights) | N/A | Reps | Weight |
| 7 | Personal Metrics | N/A | | |

| EXERCISE ID | EXERCISE TYPE ID | INTENSITY A | INTENSITY B | INTENSITY C | ... | OTHER PARAMETERS |
|---|---|---|---|---|---|---|
| $ID_1$ | TYPE($ID_1$) | INTENSITY $A_1$ | INTENSITY $B_1$ | INTENSITY $C_1$ | ... | |
| $ID_2$ | | INTENSITY $A_2$ | INTENSITY $B_2$ | INTENSITY $C_2$ | | |
| ... | ... | ... | ... | ... | | |
| $ID_N$ | TYPE($ID_N$) | INTENSITY $A_N$ | INTENSITY $B_N$ | INTENSITY $C_N$ | | |

FIG. 2

| Exercise Type ID | Exercise Class | CaloriesPerMinutePerKg= | Value 1 | Value 2 |
|---|---|---|---|---|
| 1 | Cardio (Time only) | A | TimeInMinutes | |
| 2 | Cardio (Time&Intensity) | A + (B*Val2) + (C*Val2^2) | TimeInMinutes | Intensity |
| 3 | Cardio (Time&Distance) | A + (B*(Val1/Val2)) + (C*(Val1/Val2)^2) | TimeInMinutes | Distance |
| 4 | Cardio (Pedometer) | A + (B*(Val1/Val2)) + (C*(Val1/Val2)^2) | TimeInMinutes | Distance |
| 5 | Strength (Bodyweight) | N/A | Reps | |
| 6 | Strength (with weights) | N/A | Reps | Weight |
| 7 | Personal Metrics | N/A | | |

FIG. 3

METHOD AND APPARATUS FOR COMPRESSING CALORIE BURN CALCULATION DATA USING POLYNOMIAL COEFFICIENTS

BACKGROUND OF THE INVENTION

1. Field of the Invention

This invention relates to compressing calorie burn calculations, and more particularly to a method and apparatus of using polynomials to compress calorie burn calculations.

2. Background Information

Many of todays personal goal devices, such as personal fitness planners, use calorie burn data that is provided based upon observed laboratory data. Calorie burn data is determined by many factors such as type of exercise and time of performing exercise, among others. This data is typically stored as tables of discrete data on the device in a memory. For calorie calculations that fall between recorded values, interpolation techniques are used. The storing of discrete values, however, can use a lot of system memory. On portable devices, where memory space is limited, the storing of discrete values is an inefficient use of available memory space.

BRIEF DESCRIPTION OF THE DRAWINGS

The invention is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

FIG. 2 illustrates an embodiment of the invention having a data structure in a memory to store exercise intensity polynomials.

FIG. 3 illustrates an flow diagram of an embodiment of the invention having a calorie calculation table structure.

DETAILED DESCRIPTION

The invention generally relates to an apparatus and method to reduce the amount of data required for calculating calorie burn information by using polynomial curve fitting. Referring to the figures, exemplary embodiments of the invention will now be described. The exemplary embodiments are provided to illustrate the invention and should not be construed as limiting the scope of the invention.

Figure 1:
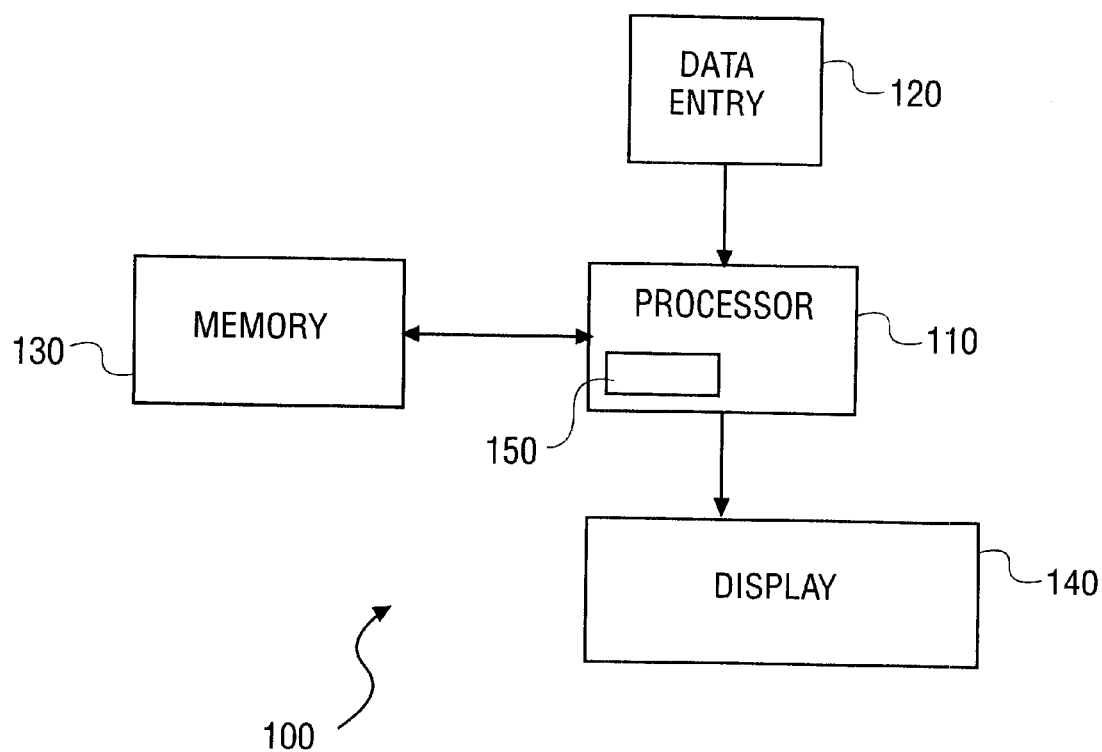
FIG. 1 illustrates an embodiment of the invention in a system.

FIG. 1 illustrates a system containing an embodiment of the invention comprising personal fitness device 100. Personal fitness device 100 comprises processor 110, data entry 120, memory 130, and display 140. Personal fitness device 100 may be may be devices such as a personal computer (PC), a personal digital assistant (PDA), a set top box (STB) or any similar type device. Data entry 120 can be entry means such as a keypad, a pointing device such as a mouse or track-ball, a touch screen, a microphone for voice recognition, or external information from other devices. In one embodiment, data entry 120 has a built in pedometer for relaying distance and time information as a user walks. Memory 130 may be memory devices such as random access memory (RAM), DRAM, or SDRAM. It should be noted that future memory devices may also be used for memory 130. Display 140 may be a display device such as an active matrix liquid crystal display (LCD) or dual-scan super-twist nematic display. Lower cost display panels with reduced resolutions and only monochrome display capabilities can also be utilized. One should note that future technology flat screen displays may also be used for display 140.

In one embodiment processor 110 contains instructions 150. In one embodiment, instructions 150 can be loaded on a PDA, a PC, a server, or be ready to be loaded onto a device in such form as a floppy disk, CD-ROM, or remotely downloaded. In one embodiment instructions 150 are used for calculating calorie burn data from polynomials based on curve fit data from the following equation:

$$Y = A + BX + CX^2$$

Instead of storing discrete observed laboratory data, three values, A, B and C, are stored. Data values A, B, and C are calorie burn calculation data such as intensity data based on a specific type of exercise. Formulas for specific exercises, such as cardiovascular type exercises (e.g., walking, jogging, biking) are used to calculate calorie burn information.

The data typically stored as discrete data is replaced by using the above equation and applying the data values, A, B, and C, to the equation. The "X" parameter in the above equation is an intensity parameter for the specific exercise type. The "X" parameter can be data such as distance and time entered by a user through data entry 120. For some exercises, the intensity level may be a constant (e.g., golf). For exercises, such as aerobics, the "X" parameter may be a number, for example a number between one (1) and ten (10). In this case, a value of one (1) would correspond to the easiest "perceived exertion" in performing the exercise, and a value of ten (10) would correspond to the hardest "perceived exertion" in performing the exercise. The perceived exertion scale is what a user perceives their level of exertion to be. One should note that other ranges of "perceived exertion" may also be implemented as well.

For exercises where distance is involved, such as running, walking, stair climbing, swimming, or biking, the "X" parameter is based on speed, i.e. time versus distance. Thus, the faster a user walks, the more calories per minute are burned. Therefore, the "X" parameter is based on inputs of time and distance. In one embodiment, a pedometer input is used to input values for parameter "X." For the pedometer inputs, since the exercise is typically walking, the pedometer supplies the values for distance and time. The "Y" parameter can be the amount of calories per minute per kilogram of weight of a user burned. One should note that other curve fit equations may also be implemented as well.

FIG. 2 illustrates a structure to store parameters of an embodiment of the invention in memory 130. Structure 200 stores data for access by an application program being executed on processor 110. Structure 200 may be an article or data object, such as a data table, array, or coupled data blocks. Structure 200 comprises a data structure including formatted blocks of entries for the following: exercise identification 210, exercise type identification 220, intensity parameter A 230, intensity parameter B 240, intensity parameter C 250, and other exercise parameters 260. In one embodiment, for a specific exercise identification 210, several exercise type identifications 220 may exist. Exercise type identification 220 may be a type of exercise dependent only upon time, dependent upon time and intensity, dependent upon time and distance, or dependent on external information, such as that information from a pedometer (e.g., distance and time).

In one embodiment, intensity parameter A 230, intensity parameter B 240, and intensity parameter C 250 are parameters based on exercise type. These parameters are dependent on a specific type of exercise and vary exercise to exercise. For each specific exercise identification 210, intensity parameters A 230, B 240, and C 250 define a curve that is used to determine calorie burn value. Intensity parameters A 230, B 240, and C 250 may be derived from observed data from standard curve fit techniques.

FIG. 3 illustrates an embodiment of the invention having a calorie calculation table based on the above equation. Calorie calculation table 300 is an article or data object for storing data for access by an application program being executed on processor 110. Calorie calculation table 300 comprises a data structure including formatted blocks of exercise type identification 310, exercise class 320, calories per minute per kilogram equations 330, value 1 340, and value 2 350. Calories per minute per kilogram equations 330 comprise the equation discussed above. In one embodiment Value 1 340 is entered through data entry 120. Value 1 340 may be time in minutes for which an exercise is performed, or repetitions of strength exercises for which the above equation is not applicable. Value 2 may be data entered through data entry 120 such as intensity a user exerted for a specific exercise, distance covered by a particular exercise, or weight used for a specific exercise.

In one embodiment of the invention calories per minute per kilogram equations 330 are computed when value 1 340 and value 2 350 are retrieved. The total amount of calories burned per exercise can then be calculated based on the following equation:

Total calories burned=Calories per minute per kilogram*duration of exercise (i.e. time)*user weight in kilograms.

The total calories burned can then be displayed on display 140.

Figure 4:
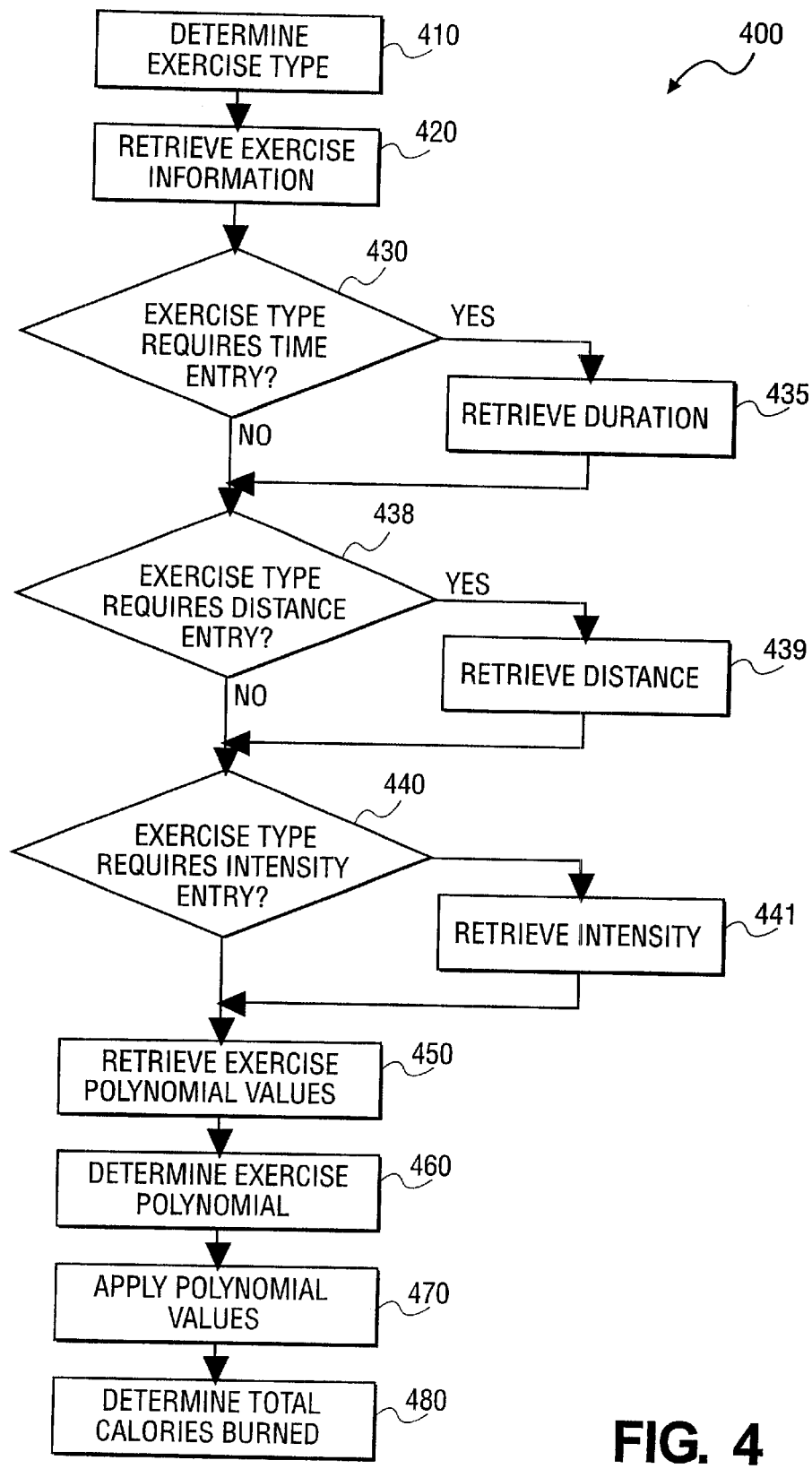
FIG. 4 illustrates a flow diagram of an embodiment of the invention.

FIG. 4 illustrates a block diagram of a process for calculating total calories burned in an embodiment of the invention. Block 410 determines an exercise that a user may have completed or desires to complete and retrieves exercise type 220. Block 420 retrieves exercise information for the specified exercise, such as exercise identification 210. Block 430 determines whether exercise type 220 requires an entry for duration information. If exercise type 220 does not require an entry for duration information, process 400 continues with block 438. If exercise type 220 requires an entry for duration information, block 435 retrieves duration entered by a user or duration from a device such as a pedometer. Block 438 determines if exercise type 220 requires distance information. If exercise type 220 does not require distance information, process 400 continues with block 440. If exercise type 220 requires an entry for distance information, block 439 retrieves distance information entered by a user or distance information from a device such as a pedometer. Block 440 determines if exercise type 220 requires exercise intensity (e.g., scale of 1–10) information. If exercise type 220 requires exercise intensity information, block 441 retrieves intensity information entered by a user. If exercise type 220 does not require intensity information, process 400 continues with block 450. Block 450 retrieves intensity parameter A 230, intensity parameter B 240, and intensity parameter C 250, exercise type identification 210, and exercise type identification 220 based on retrieved exercise information entered by a user. Block 460 looks up exercise type identification 210 and determines the correct calories per minute per kilogram equation 330 to apply. Block 470 determines calories per minute per kilogram. Block 480 determines total calories burned.

Figure 5:
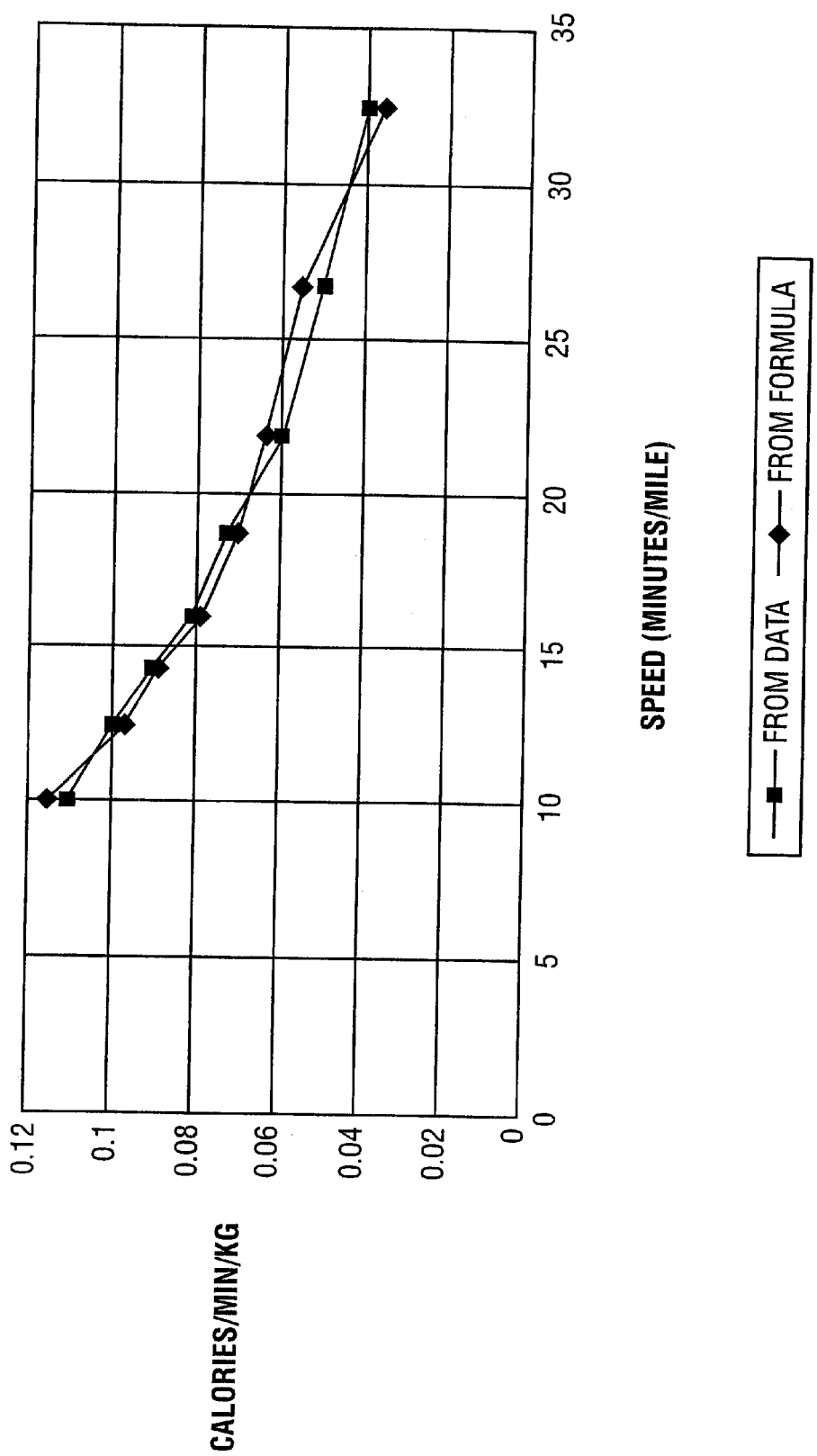
FIG. 5 illustrates an example of an embodiment of the invention's calculation versus observed data.

FIG. 5 illustrates an example of data determined by an embodiment of the invention for an exercise as compared to observed laboratory data. As one can observe from FIG. 5, the data determined by an embodiment of the invention is a very close approximation of the observed data.

Figure 6:
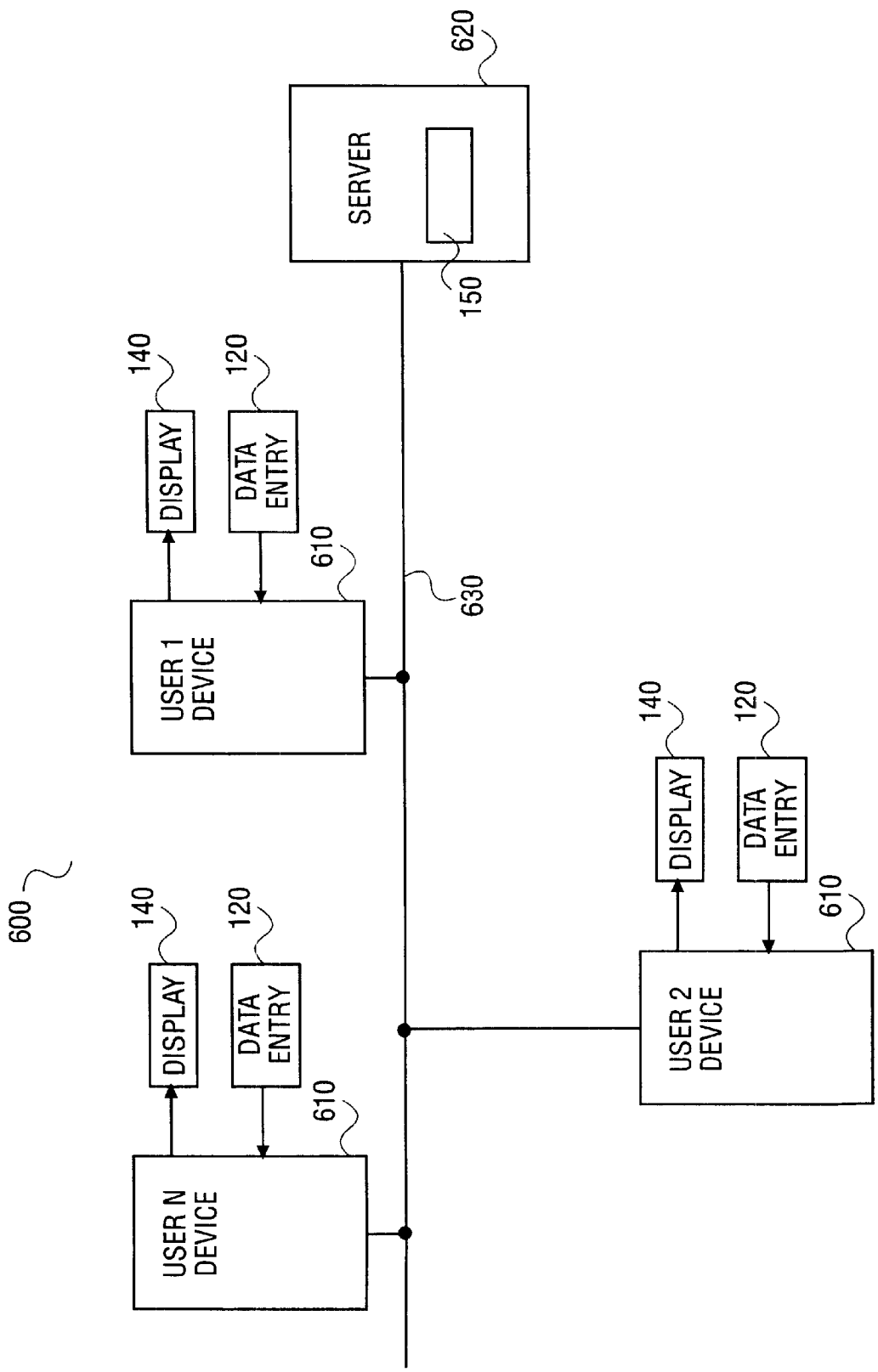
FIG. 6 illustrates an example of an embodiment of the invention in a network environment using remote devices to connect to a server.

FIG. 6 illustrates an embodiment of the invention that can run on a server and be accessed by a user at a remote location. Server 620 can calculate calorie burn information through instructions 150. A user can enter exercise information through data entry 120. Display 140 then displays entered information and resulting calories burned for entered data. User device 610 may be devices such as a PC, a PDA, a STB or any similar device. In one embodiment of the invention, multiple users may be compared against for comparison in situations, such as a fitness class. These multiple users can connect to server 610 through a network, such as the Internet, or an intranet. In this way, all members in a fitness class can keep track of burned calories during periods of time.

Also, a fitness device, such as a cross-trainer, exercise bike, or stepping machine can be used for multiple users and a set intensity can be entered on user device 610 for comparison of multiple users in a center situated class or remotely. The results can then be centrally stored and compared over time. This data can then be used for multiple purposes such as contests, medical research, and fitness goals. Therefore, with a large number of users, the reduction of memory space by using polynomial values for calorie burn calculation is much more efficient than storing observed data and also results in a cost savings by reducing necessary memory space.

Therefore, by employing a curve fit equation and fewer parameters, memory is more efficiently used than having to store observed data. With the efficient use of memory, memory 130 is able to store more information without compromising calorie burn results. This also saves cost by reducing memory size.

The above embodiments can also be stored on a device or medium and read by a machine to perform instructions. The device or medium may include a solid state memory device and/or a rotating magnetic or optical disk. The device or medium may be distributed when partitions of instructions have been separated into different machines, such as across an interconnection of computers.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. An apparatus comprising:
   a processor; and
   a memory coupled to the processor, the processor to calculate calorie burn and the memory having a plurality of data objects to store data for access by an application program being executed on the processor comprising:
      a first data structure stored in one of the plurality of data objects, the first data structure including a formatted exercise data block used by the application program, the formatted exercise data block including a plurality of formatted exercise intensity data blocks having polynomial parameters, and a second data structure stored in another one of the plurality of data objects, the second data structure including a formatted calorie calculation block used by the application program, wherein the formatted calorie calculation block comprises a plurality of exercise intensity information blocks including exercise perceived intensity information.

2. The apparatus of claim 1, wherein calorie burn is calculated by curve fit.

3. The apparatus of claim 1, wherein the formatted exercise data block further comprises:
   a plurality of identification data blocks; and
   a plurality of exercise type data blocks.

4. The apparatus of claim 3, wherein the exercise data block comprises information for a plurality of exercises.

5. The apparatus of claim 3, wherein polynomial parameters are derived from a curve fit polynomial.

6. The apparatus of claim 1, wherein the formatted calorie calculation block further comprises:
   an exercise type identification block;
   an exercise class block; and
   a calorie calculation block.

7. The apparatus of claim 6, wherein the formatted calorie calculation block comprises information for a plurality of exercises.

8. The apparatus of claim 6, wherein the calorie calculation block comprises a polynomial curve fit equation.

9. The apparatus of claim 6, wherein the plurality of exercise intensity information blocks further comprises one of exercise duration information, exercise distance information, exercise weight information and exercise repetition information.

10. A method comprising:
    determining an exercise type;
    retrieving exercise information;
    retrieving a plurality of exercise polynomials;
    applying the plurality of exercise polynomials to one of a plurality of calorie equations; and
    calculating total calories burned,
    wherein the plurality of calorie equations are stored on a data object for access by an application program being executed on a processor, the data object comprising:
      a data structure having a formatted calorie calculation block used by the application program including a plurality of exercise intensity information blocks comprising exercise perceived intensity information.

11. The method of claim 10, wherein the plurality of exercise polynomials are stored on a data object for access by an application program being executed on a processor, the data object comprising:
    a data structure having a formatted exercise data block used by the application program.

12. The method of claim 11, wherein the formatted exercise data block comprises:
    a plurality of formatted exercise intensity data blocks;
    a plurality of identification data blocks; and
    a plurality of exercise type data blocks.

13. The method of claim 11, wherein the exercise data block comprises information for a plurality of exercises.

14. The method of claim 12, wherein the plurality of formatted exercise intensity data blocks comprises polynomial parameters derived from a curve fit polynomial.

15. The method of claim 10, wherein the formatted calorie calculation block comprises:
    a plurality of exercise type identification blocks;
    a plurality of exercise class blocks; and
    a plurality of calorie equation blocks.

16. The method of claim 15, wherein the formatted calorie calculation block comprises information for a plurality of exercises.

17. The method of claim 16, wherein the plurality of calorie equation blocks comprise a plurality of polynomial curve fit equations.

18. The method of claim 15, wherein the plurality of exercise intensity data blocks further comprises one of exercise duration information, exercise distance information, exercise weight information and exercise repetition information.

19. A program storage device readable by a machine comprising instructions that cause the machine to:
    determine an exercise type;
    retrieve exercise information;
    retrieve a plurality of exercise polynomials;
    apply the plurality of exercise polynomials to one of a plurality of calorie equations; and
    calculate total calories burned,
    wherein the plurality of calorie equations are stored on a data object for access by an application program being on a processor, the data object comprising:
      a data structure having a formatted calorie calculation block used by the application program including a plurality of exercise intensity information blocks comprising exercise perceived intensity information.

20. The program storage device of claim 19, wherein the plurality of exercise polynomials are stored on a data object for access by an application program being executed on a processor, the data object comprising:
    a data structure having a formatted exercise data block used by the application program.

21. The program storage device of claim 20, wherein the formatted exercise data block comprises:
    a plurality of formatted exercise intensity data blocks;
    a plurality of identification data blocks; and
    a plurality of exercise type data blocks.

22. The program storage device of claim 20, wherein the formatted exercise data block comprises information for a plurality of exercises.

23. The program storage device of claim 22, wherein the plurality of formatted exercise intensity data blocks comprise polynomial parameters derived from a curve fit polynomial.

24. The program storage device of claim 19, wherein the formatted calorie calculation block comprises:
    a plurality of exercise type identification blocks;
    a plurality of exercise class blocks; and
    a plurality of calorie equation blocks.

25. The program storage device of claim 24, wherein the formatted calorie calculation block comprises information for a plurality of exercises.

26. The program storage device of claim 24, wherein the plurality of calorie equation blocks comprise a plurality of polynomial curve fit equations.

27. The program storage device of claim 19, wherein the plurality of exercise intensity information blocks further comprises one of exercise duration information, exercise distance information, exercise weight information and exercise repetition information.

* * * * *